US007019828B2

(12) United States Patent
Su et al.

(10) Patent No.: US 7,019,828 B2
(45) Date of Patent: Mar. 28, 2006

(54) CHEMICAL ENHANCEMENT IN SURFACE ENHANCED RAMAN SCATTERING USING LITHIUM SALTS

(75) Inventors: Xing Su, Cupertino, CA (US); Lei Sun, Santa Clara, CA (US); Tae-Woong Koo, South San Francisco, CA (US); Selena Chan, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 160 days.

(21) Appl. No.: 10/387,080

(22) Filed: Mar. 12, 2003

(65) Prior Publication Data

US 2004/0179195 A1  Sep. 16, 2004

(51) Int. Cl.
G01J 3/44 (2006.01)
(52) U.S. Cl. .................................. 356/301; 356/303
(58) Field of Classification Search ................ 356/301; 435/6, 287.2, 287.9
See application file for complete search history.

(56) References Cited

U.S. PATENT DOCUMENTS

| 6,174,677 | B1 * | 1/2001 | Vo-Dinh ........................ 435/6 |
| 6,623,977 | B1 * | 9/2003 | Farquharson et al. ....... 436/164 |
| 2003/0129608 | A1 * | 7/2003 | Mirkin et al. .................. 435/6 |
| 2003/0211488 | A1 | 11/2003 | Mirkin et al. |

FOREIGN PATENT DOCUMENTS

| WO | WO 02/099982 A2 | 12/2002 |
| WO | WO 2004/031749 A2 | 4/2004 |

OTHER PUBLICATIONS

PCT International Search Report (dated Sep. 29, 2004), International Application No. PCT/US2004/002989—International Filing Date Apr. 2, 2004 (19 pages).

Jong-Jean Kim, et al., "Surface-Enhanced Ramona Scattering of Pyridine and Benzene in Non-Aqueous Electrochemical Systems of Alcoholic Solvents", Chemical Physics Letters Aug. 1985, Netherlands, vol. 118, No. 5, XP009036269, ISSN: 0009-2614 (pp. 493-497).

Quatrain Kneipp, et al., "Single Molecule Detection Using Surface-Enhanced Raman Scattering (SERS)", Physical Review Letters, New York, USA, Mar. 3, 1997, vol. 78, No. 9, XP002106891, ISSN: 0031-9007 (pp. 1667-1670).

A. Kudelski, et al., "Surface-Enhanced Raman Scattering (SERS) at Copper(I) Oxide", Journal of Raman Spectroscopy, May 1998, Wiley, UK, vol. 29, No. 5, XP002296356, ISSN: 0377-0486 (pp. 431-435).

(Continued)

Primary Examiner—Layla G. Lauchman
(74) Attorney, Agent, or Firm—Julia A. Hodge

(57) ABSTRACT

Briefly, in accordance with one embodiment of the invention, the intensity of the signals from surface enhanced Raman spectroscopy may be increased by using lithium chloride as an enhancer to activate a metallic structure used for surface enhanced Raman spectroscopy. The increased signal intensity may allow surface enhanced Raman spectroscopy to be utilized to detect individual analytes such as nucleotides, for example in DNA sequencing without requiring a dye or radioactive label.

16 Claims, 4 Drawing Sheets

OTHER PUBLICATIONS

A. Kudelski, et al., "Characterization of the Copper Surface Optimized for Use as a Substrate for Surface-Enhanced Raman Scattering", Vibrational Spectroscopy, Mar. 1998, Elsevier, Netherlands, vol. 16, No. 1, XP002296357, ISSN: 0924-2031 (pp. 21-29).

Antonio Grondin, et al., "Benzotriazole Maleimide as a Bifunctional Reactant for SERS", J. Chem. Soc., Perkin Trans., vol. 2, Sep. 2001, P002296358, (pp. 2136-2141).

Selena Chan, et al., "Surface-Enhanced Raman Scattering of Small Molecules From Silver-Coated Silicon Nanopores", Advanced Materials, Oct. 2, 2003, vol. 15, No. 19, XP002296359 (pp. 1595-1598).

Narayana R. Isola, et al., "Surface-Enhanced Raman Gene Probe for HIV Detection", Advanced Monitoring Development Group, Life Sciences Division, Oak Ridge National Laboratory, Tennessee, USA, Analytical Chemistry, vol. 70, No. 7, Apr. 1, 1998 (pp. 1352-1356).

T. Vo-Dinh et al., "Surface-Enhanced Raman Scattering (SERS) Method and Instrumentation for Genomics and Biomedical Analysis", Advanced Monitoring Development Group, Life Sciences Division, Oak Ridge National Laboratory, Tennessee, USA, Journal of Raman Spectroscopy 30, Accepted Jun. 14, 1999 (pp. 785-793).

Jing Ni, et al., "Immunoassay Readout Method Using Extrinsic Raman Labels Adsorbed on Immunogold Colloids", Microanalytical Instrumentation Center, Ames Laboratory—USDOE, and Department of Chemistry, Iowa State University, Iowa, USA, Analytical Chemistry, vol. 71, No. 21, Nov. 1, 1999 (pp. 4903-4908).

Duncan Graham, et al., "Simple Multiplex Genotyping by Surface-Enhanced Resonance Raman Scattering" Department of Pure and Applied Chemistry, University of Strathclyde, Glasgow, U.K., Analytical Chemistry, vol. 74, No. 5, Mar. 1, 2002 (pp. 1069-1074).

Yun Wei Charles Cao, et al., "Nanoparticles with Raman Spectroscopic Fingerprints for DNA and RNA Detection", Department of Chemistry and Institute for Nanotechnology, Northwestern University, Illinois, USA, Science vol. 297, Aug. 30, 2002, www.sciencemag.org (pp. 1536-1540).

William E. Doering, et al., "Spectroscopic Tags Using Dye-Embedded Nanoparticles and Surface-Enhanced Raman Scattering", Departments of Biomedical Engineering and Chemistry, Emory University and Georgia Institute of Technology, Georgia, USA, Analytical Chemistry, Accepted Sep. 4, 2003 (pp. A-F).

Desiree S. Grubisha, et al., "Femtomolar Detection of Prostate-Specific Antigen: An Immunoassay Based on Surface-Enhanced Raman Scattering and Immunogold Labels", Microanalytical Instrumentation Center, Ames Laboratory—USDOE, and Department of Chemistry, Iowa State University, Iowa, USA, Analytical Chemistry, vol. 75, No. 21, Nov. 1, 2003 (pp. 5936-5943).

* cited by examiner

US 7,019,828 B2

CHEMICAL ENHANCEMENT IN SURFACE ENHANCED RAMAN SCATTERING USING LITHIUM SALTS

CROSS-REFERENCE TO RELATED APPLICATIONS

The present application claims the benefit of provisional application Express Mail Label number EV 154 573 591 US (serial number not yet assigned) filed on Mar. 3, 2003.

BACKGROUND OF THE INVENTION

The sensitive and accurate detection or identification of individual molecules from biological and other samples has proven to be an elusive goal, with widespread potential uses in medical diagnostics, pathology, toxicology, environmental sampling, chemical analysis, forensics and numerous other fields. Attempts have been made to use Raman spectroscopy or surface plasmon resonance to achieve this goal. When light passes through a medium of interest, a certain amount of the light becomes diverted from its original direction in a phenomenon known as scattering. Some of the scattered light also differs in frequency from the original excitatory light, due to the absorption of light and excitation of electrons to a higher energy state, followed by light emission at a different wavelength. The difference of the energy of the absorbed light and the energy of the emitted light matches the vibrational energy of the medium. This phenomenon is known as Raman scattering, and the method to characterize and analyze the medium or molecule of interest with the Raman scattered light is called Raman spectroscopy. The wavelengths of the Raman emission spectrum are characteristic of the chemical composition and structure of the Raman scattering molecules in a sample, while the intensity of Raman scattered light is dependent on the concentration of molecules in the sample.

The probability of Raman interaction occurring between an excitatory light beam and an individual molecule in a sample is very low, resulting in a low sensitivity and limited applicability of Raman analysis. It has been observed that molecules near roughened silver surfaces show enhanced Raman scattering of as much as two orders of magnitude or more. This surface enhanced Raman scattering (SERS) effect is related to the phenomenon of plasmon resonance, wherein metal nanoparticles or metal coatings exhibit a pronounced optical resonance in response to incident electromagnetic radiation, due to the collective coupling of conduction electrons in the metal. In essence, nanoparticles of gold, silver, copper and certain other metals can function to enhance the localized effects of electromagnetic radiation. Molecules located in the vicinity of such particles exhibit a much greater sensitivity for Raman spectroscopic analysis. Surface enhanced Raman spectroscopy (SERS) is the technique to utilize surface enhanced Raman scattering effect to characterize and analyze the medium or molecule of interest.

Attempts have been made to exploit SERS for molecular detection and analysis, typically by utilizing metal nanoparticles or fabricating rough metal films on the surface of a substrate and then applying a sample to the metal nanoparticles in liquid or the metal-coated surface. However, the metal particles can aggregate to yield stronger resonance, and the enhancement factor with the metal particles is, in general, higher than that with the metal-coated surface. To date, sodium chloride has been identified as a chemical that overall enhances the SERS signal when applied to the metal nanoparticles or metal-coated surfaces before or after the molecule of interest is introduced. However, using sodium chloride as an enhancer has not been sensitive enough to detect lower concentrations of target molecules such as single nucleotides reliably, and as a result SERS has not been suitable for DNA sequencing. Thus, there lies a need to reliably detect individual molecules such as nucleotides using a SERS process.

DESCRIPTION OF THE DRAWING FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
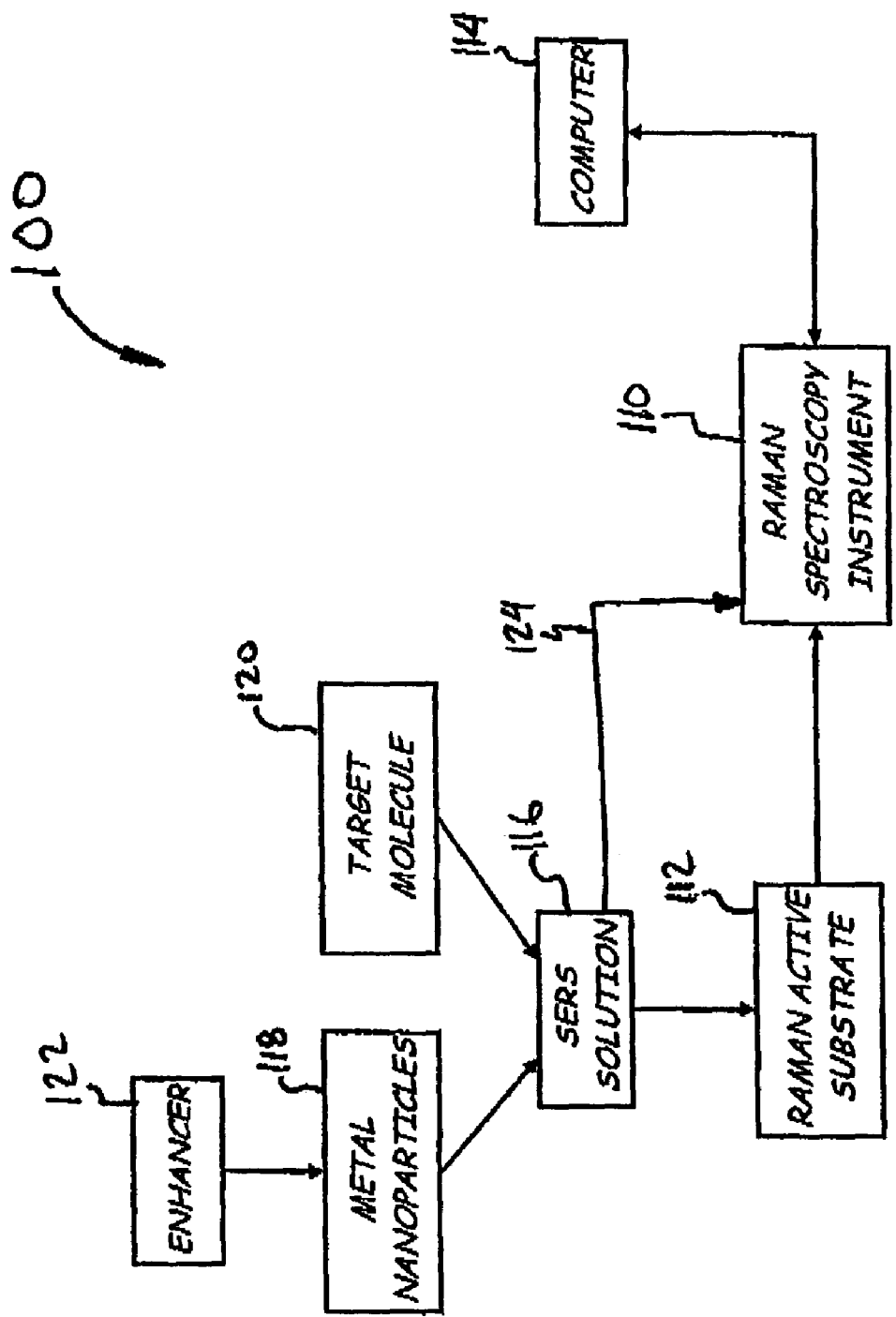
FIG. 1 is a block diagram of an overall surface-enhanced Raman spectroscopy system in accordance with one embodiment of the present invention.

It will be appreciated that for simplicity and clarity of illustration, elements illustrated in the figures have not necessarily been drawn to scale. For example, the dimensions of some of the elements are exaggerated relative to other elements for clarity. Further, where considered appropriate, reference numerals have been repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

As utilized herein, the term analyte may mean any atom, chemical, molecule, compound, composition or aggregate of interest for detection or identification although the scope of the invention is not limited in this respect. Non-limiting examples of analytes may include, but are not limited to, an amino acid, peptide, polypeptide, protein, glycoprotein, lipoprotein, nucleoside, nucleotide, oligonucleotide, nucleic acid, deoxyribose nucleic acid, ribose nucleic acid, peptide nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, bacteria, virus, radioisotope, vitamin, heterocyclic aromatic compound, carcinogen, mutagen, narcotic, amphetamine, barbiturate, hallucinogen, waste product, contaminant, quantum dots, or dyes. In certain embodiments of the invention, one or more analytes of weaker Raman signals may be labeled with or adsorbed to one or more molecules of stronger Raman signal, as disclosed below, although the scope of the invention is not limited in this respect. In this case, the molecule of stronger Raman signal is called a Raman label or Raman tag.

In the following description and claims, the terms coupled and connected, along with their derivatives, may be used. It should be understood that these terms are not intended as synonyms for each other. Rather, in particular embodiments, connected may be used to indicate that two or more elements are in direct physical or electrical contact with each other. Coupled may mean that two or more elements are in direct physical or electrical contact. However, coupled may also mean that two or more elements are not in direct contact with each other, but yet still cooperate or interact with each other.

Referring now to FIG. 1, a block diagram of an overall system for surface-enhanced Raman spectroscopy (SERS) will be discussed. As shown in FIG. 1, SERS system 100 may include a Raman spectroscopy instrument 110 for analyzing molecules disposed on a Raman active substrate 112. Raman active substrate 112 may include a substrate that is suitable for Raman spectroscopy. In one particular embodiment, Raman active substrate 112 may be a SERS active substrate in that the substrate is suitable for SERS analysis, although the scope of the invention is not limited in this respect. A computer 114 may be utilized to control the operation of Raman spectroscopy instrument 110, to receive an output from Raman spectroscopy instrument 110, and to compile, display, store, or otherwise organize and present a result of a Raman spectroscopy analysis provided by Raman spectroscopy instrument 110, although the scope of the invention is not limited in this respect.

Raman active substrate 112 may be produced from a SERS solution 116 which may be prepared by combining metal nanoparticles 118 used for Raman spectroscopy enhancement with a target molecule 120 to be detected with Raman spectroscopy instrument 110. In at least one embodiment, the term metal or metal nanoparticles may in general refer to and may encompass any metallic structure which may include any structure made wholly, partially, in mixture, or in layers of metal, and which may include rough metal, metal colloids, metal nanoparticles, metal films, and metal coatings, although the scope of the invention is not limited in this respect. In one embodiment of the invention, the metal nanoparticles 118 may be enhanced or activated using an enhancer 122 that operates to further improve the enhancing effect of the metal nanoparticles 118 by increasing the Raman scattering intensity of the analyte, although the scope of the invention is not limited in this respect. Thus, enhancer 122 may be utilized to activate the metallic structure used in SERS to increase the overall enhancing effect of the SERS metallic structure. The enhancer 122 may be used before or after the target molecule in introduced to the metal nanoparticles. In one embodiment of the invention, SERS solution 116 may be utilized to produce a Raman active substrate 112 by deposition of the SERS solution 116 onto the substrate, which may be inserted into Raman spectroscopy instrument 110 for analysis, although the scope of the invention is not limited in this respect. In one embodiment of the invention, the Raman active substrate is obtained by utilizing a metal-coated substrate, using enhancer 122, and introducing target molecule 120. In one particular embodiment of the invention, Raman active substrate 112 is not used, and a solution of a target molecule 120 and metal nanoparticles 118 enhanced or activated by enhancer 122 is directly analyzed in Raman spectroscopy instrument 110, although the scope of the invention is not limited in this respect. Such an arrangement is shown by optional path 124 by which SERS solution 116 is analyzed directly by Raman spectroscopy instrument 110 without requiring Raman active substrate 112.

Figure 2:
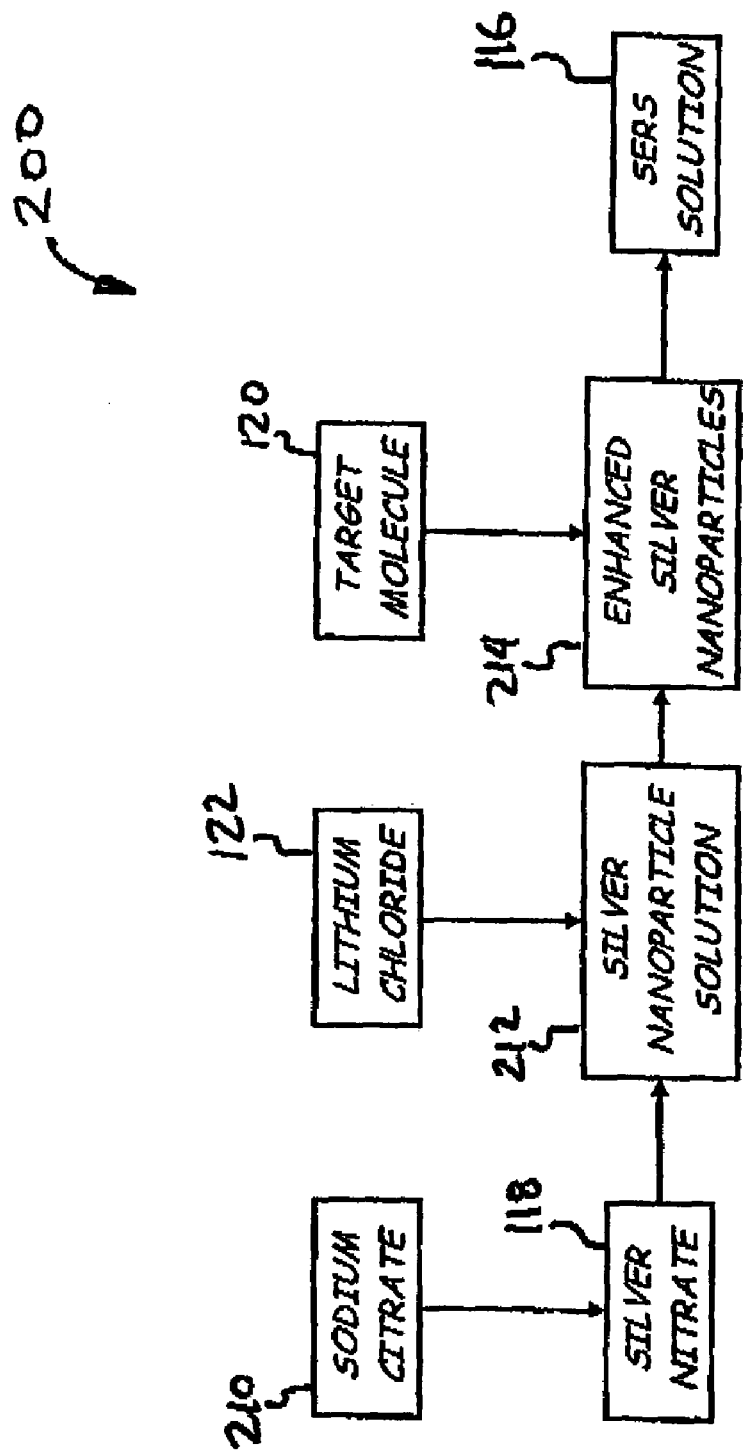
FIG. 2 is a block diagram of a method for producing a solution for surface-enhanced Raman spectroscopy in accordance with one embodiment of the present invention.

Referring now to FIG. 2, a flow diagram of a process for producing a solution for surface-enhanced Raman spectroscopy (SERS) in accordance with the present invention will be discussed. The process 200 for producing SERS solution 116 may include preparing metal nanoparticles for SERS analysis. In one embodiment of the invention, the metal nanoparticles 118 may include silver, gold, copper, or any other metal or metallic structure, or a combination of the metals or metallic structures, although the scope of the invention is not limited in this respect. In one particular, but non-limiting, embodiment, a silver nanoparticle solution 212 may be prepared using the following described method. Silver nitrate 118 is added to ultra pure water in a reflux flask with a stir bar. In one embodiment, for example, 0.2 milliliters of silver nitrate in 85 milligrams per milliliter solution is added to 97 milliliters of ultra pure water. A reflux apparatus including the reflux flask is assembled over a hotplate and the temperature is set 400 degrees Celsius to heat the liquid in the reflux flask. A solution of sodium citrate 210 is prepared, for example 0.2 milliliters of sodium citrate of 100 milligrams per milliliter concentration is diluted with water to a final volume of 2 milliliters in a 50-milliliter plastic tube. The sodium citrate solution is then added drop-wise to the boiling silver solution in the reflux flask over a five-minute period while stirring the silver solution at 350 revolutions per minute. The silver solution is refluxed for approximately one hour. After reflux, the solution is cooled, and the volume is adjusted to 100 milliliters and transferred to a glass bottle for storage of the resulting silver nanoparticle solution 212 at room temperature without exposure to direct sunlight. In other embodiments, the metal nanoparticles may be made by laser ablation, mechanical grinding, or chemical etching of metals, although the scope of the invention is not limited in this respect. The size of the metal nanoparticles in solution in one embodiment is approximately in the 50 to 100 nanometer range. It should be noted that the scope of the invention is not limited in any respect by the thus described process.

In one, non-limiting, embodiment of the invention, the silver nanoparticle solution 212 may be prepared for SERS analysis via the following procedure. Lithium chloride may be used as enhancer 122, which is added to the silver nanoparticle solution at a final concentration of 0.18 M to enhance the metal nanoparticles in the silver nanoparticle solution 212 to arrive at a solution of enhanced silver nanoparticles 214. A target molecule 120 is then added to the enhanced silver nanoparticle solution 214 to arrive at the SERS solution 116. In one embodiment of the invention, the target molecule may be any analyte of interest for analysis using Raman spectroscopy or SERS or the like. In one non-limiting embodiment of the invention, deoxyadenosine monophosphate (dAMP) was selected as the target molecule 120. In one embodiment of the invention, target molecule 120 may include a mixture of different types of analytes. In one particular embodiment of the invention, approximately 200 microliters of the SERS solution 116 was placed into a Raman spectroscopy instrument 110. In one particular embodiment of the invention, target molecule 120 may be added to the silver nanoparticle solution, and then the lithium chloride 122 is added to the mixture of the silver nanoparticle solution and the target molecule. In certain embodiments of the invention, the SERS solution 116 may be added to a porous silicon substrate to produce a Raman activate substrate suitable for use in a Raman spectroscopy instrument 110, although the scope of the invention is not limited in this respect. It should be noted that although one example is shown in FIG. 2, the order in which nanoparticles 118, enhancer 122, and target molecule 120 are mixed may vary, so that the scope of the invention is not limited to any order of combining.

Figure 3:
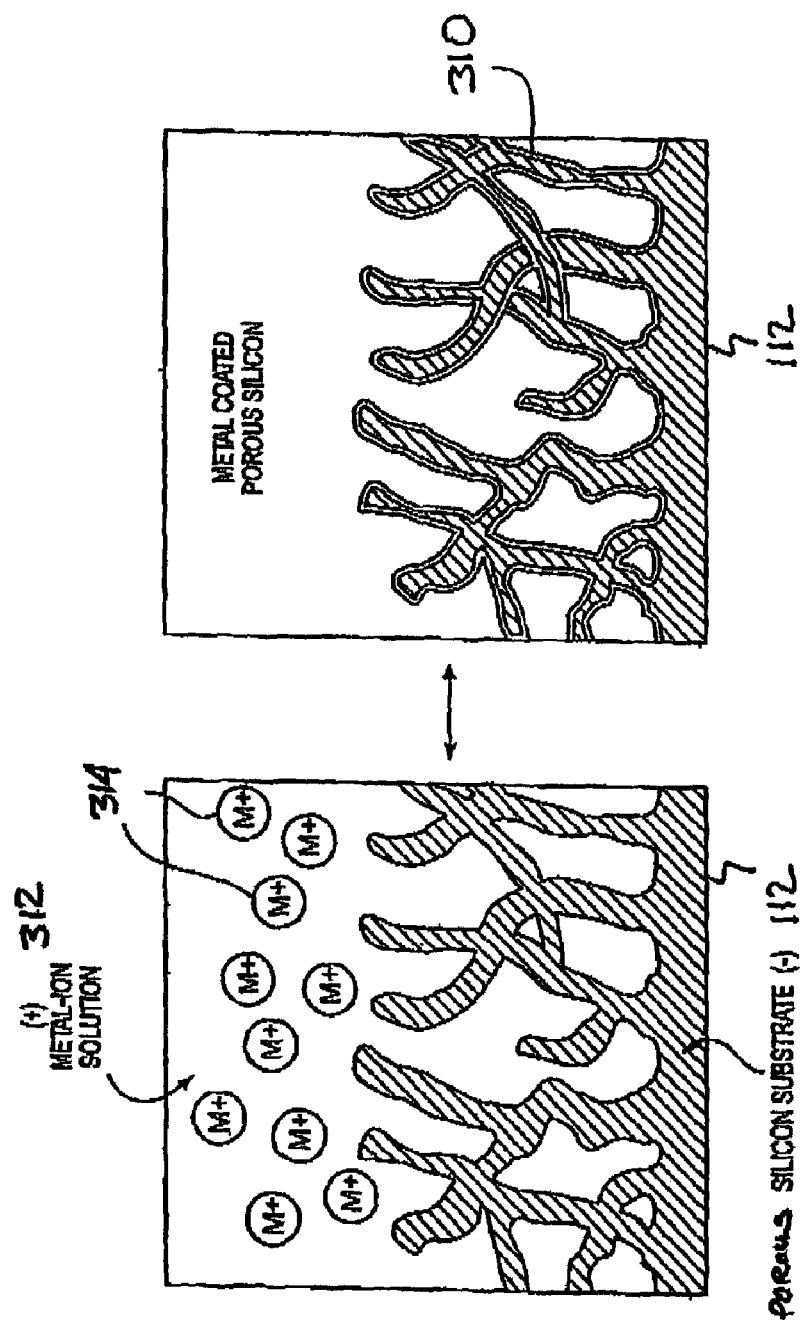
FIG. 3 is a diagram of a porous silicon substrate suitable for surface enhanced Raman spectroscopy in accordance with one embodiment of the present invention.

Referring now to FIG. 3, a silicon substrate suitable for use as a Raman active substrate in accordance with an embodiment of the invention will be discussed. Substrate 112 may comprise a silicon substrate to which a metal ion solution 312 containing metal ions 314 may be added in order to form a layer of metallic layer 310 on substrate 112. In one embodiment of the invention, substrate 112 may comprise nanocrystalline silicon which may refer to silicon that comprises nanometer scale silicon crystals, for example in the range of 1 to 100 nanometers (nm), including but not limited to porous silicon, although the scope of the invention is not limited in this respect. In another embodiment of the invention, substrate 112 may comprise porous silicon which may refer to silicon that has been etched or otherwise treated to form a porous structure. Other types of silicon substrates formed using various processes may also be utilized without departing from the scope of the invention, and without providing a substantial change thereto. As an example, substrate 112 may alternatively comprise silicon nitride, germanium, silicon carbide, gallium arsenide, indium phosphate, or silicon oxide, and may include minor amounts of other materials such as metal nucleation catalysts and dopants, although the scope of the invention is not limited in this respect.

As shown in FIG. 3, substrate 112 may be coated with a Raman active metallic structure, such as gold, silver, platinum, copper or aluminum, for example, as utilized in SERS solution 116. The composition and thickness of the metal layer 310 may be controlled to optimize the plasmon resonant frequency of substrate 112 as desired. In one embodiment of the invention, metal layer 310 may be composed of metal colloid, or any other metallic structure, of gold or silver nanoparticles in accordance with the present invention, which may be suitable for detection of smaller sized target molecule analytes such a single nucleotides or amino acids, although the scope of the invention is not limited in this respect. In one embodiment of the invention, a solution of nanoparticles such as SERS solution 116 may be added to a substrate 112 already having a metal layer 310 disposed thereon in order to enhance the Raman signal in accordance with surface enhanced Raman spectroscopy. In a particular embodiment of the invention, substrate 112 may be incorporated into a larger apparatus, system, or article of manufacture such as a micro-electromechanical system (MEMS), which in one embodiment may refer to integrated systems comprising mechanical elements, sensors, actuators, electronics, and so on, although the scope of the invention is not limited in this respect. Such a MEMS system may be utilized to measure or manipulate, for example, mechanical, thermal, biological chemical, physical, optical, electrical, or magnetic phenomena.

Although FIG. 3 shows one type of substrate that may be utilized for Raman active substrate 112, various other types of substrates may be utilized. For example, in one embodiment Raman active substrate 112 may comprise a metal nanoparticle island film that consists of isolated metal nanoparticles deposited on a base substrate. In an alternative embodiment, Raman active substrate 112 may comprise a metal-coated nanoparticle based substrate consists of a base substrate covered with nanoparticles in a first layer and then coated with a continuous layer of a SERS metal or metallic structure such as gold, silver, copper, platinum, aluminum or the like. In yet another embodiment, Raman active substrate may comprise a polymer film with embedded nanoparticles. The polymer film may be disposed as a layer on a base substrate. The base substrate itself may comprise various materials, including but not limited to silicon, glass or quartz, or cellulose or paper based material, although the scope of the invention is not limited in this respect.

Figure 4:
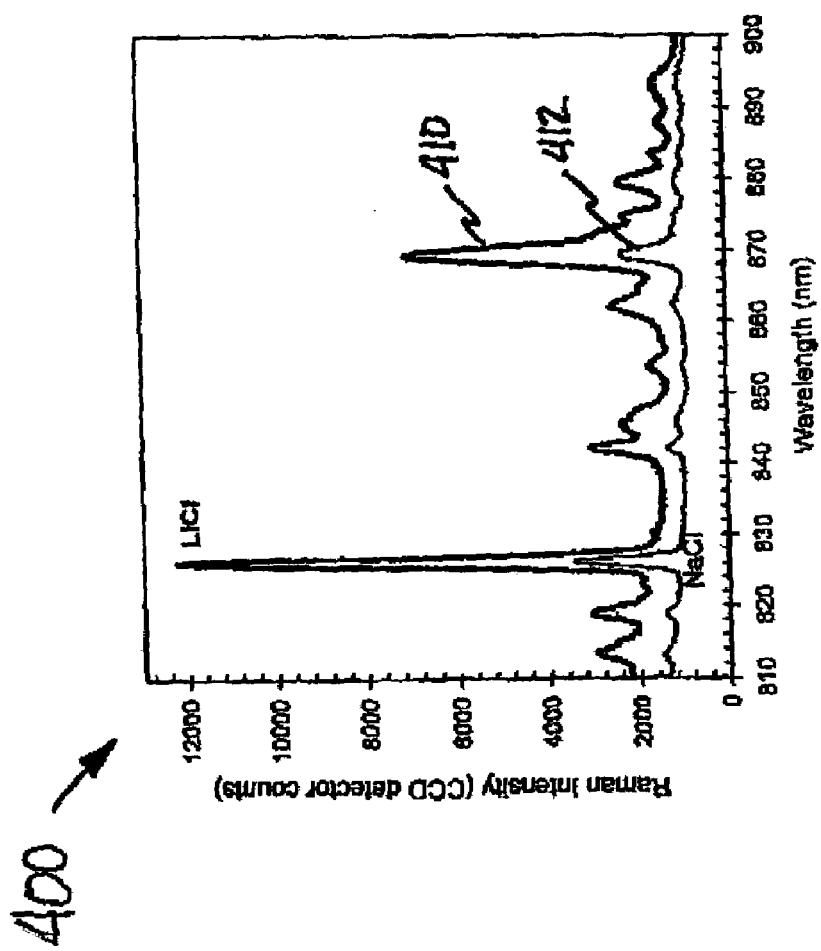
FIG. 4 is a graphical representation of SERS spectra in accordance with an embodiment of the present invention.

Referring now to FIG. 4, a graphical representation of Raman signal intensity versus wavelength in accordance with one embodiment of the invention will be discussed. Plot 400 shows Raman signal intensity of a SERS process on the vertical axis as measured by the counts of a charge coupled device (CCD) of Raman spectroscopy instrument 110, versus the wavelength of the Raman scattered light on the horizontal axis, in nanometer units. The signals 410 and 412 shown in plot 400 were generated by using dAMP as target molecule 120 with excitation light of 785 nanometers in wavelength in accordance with the procedure described herein. In one case, sodium chloride was used as enhancer 122, and the resulting spectrum is shown at 412. In another case, lithium chloride was used as enhancer 122 in accordance with the present invention, and the resulting spectrum is shown at 410. As can be seen from plot 400, the intensity of the lithium chloride spectrum 410 is greater than the intensity of the sodium chloride spectrum 412. With such an increased Raman signal intensity using lithium chloride as an enhancer 122 for a SERS process, detection of single molecules such as individual nucleotides may be achieved so that SERS may be utilized, for example, in DNA sequencing without requiring the use of labels, although the scope of the invention is not limited in this respect.

The selection of inorganic salts may help to optimize chemical enhancement effects in SERS. In accordance with one embodiment of the invention, the investigation of the ionic effect consisted of screening 18 salts against three classes of target molecules: nucleotides, nucleosides, and bases. Even when the same anion is used, it has been discovered that different cations may affect the SERS signal significantly. It has been particularly discovered that lithium chloride (LiCl) may provide a SERS signals of greater intensity than other salts such as sodium chloride (NaCl). Thus, the selection of the cation in an enhancer may result in enhanced SERS signal intensity. It has been discovered that a strong SERS enhancement with LiCl may be particularly suitable for at least one group of target molecules. When ions are introduced into colloidal solutions, the colloidal particles may form aggregates and alter the electromagnetic enhancement of the SERS process. The increased SERS signal intensity was observed to occur at multiple wavelengths, including both the visible and near-infrared spectrum, for example at 514 nm, 785 nm, and 830 nm. These observed results suggest that the Raman enhancement resulting from LiCl is not solely due to an electromagnetic effect which is sensitive to the excitation wavelength.

The knowledge of specific molecular structures for strong SERS signals using LiCl may be applied to the design and selection of tag molecules that can provide a strong SERS signals. DNA fragments may be detected using LiCl enhanced SERS so that Raman tag molecules may be manufactured by modifying structures of simple biomolecules without requiring the use of dye molecules or radioactive labels. Compact optical tag molecules may exhibit compatibility with proteins, and the use of optical tag molecules in chemical reactions such as polymerase chain reaction and nuclease activity may promote further opportunity for optical observation of biological phenomena using LiCl enhanced SERS.

Although the invention has been described with a certain degree of particularity, it should be recognized that elements thereof may be altered by persons skilled in the art without departing from the spirit and scope of the invention. It is believed that the chemical enhancement in surface enhanced Raman scattering using lithium salts or the like of the present invention and many of its attendant advantages will be understood by the forgoing description, and it will be apparent that various changes may be made in the form, construction and arrangement of the components thereof without departing from the scope and spirit of the invention or without sacrificing all of its material advantages, the form herein before described being merely an explanatory embodiment thereof, and further without providing substantial change thereto. It is the intention of the claims to encompass and include such changes.

What is claimed is:

1. A method for analyzing a sample by surface enhanced Raman spectroscopy (SERS) comprising:
    providing a solution of silver nanoparticles;
    creating an enhanced silver nanoparticle solution by adding lithium chloride to the silver nanoparticle solution;
    contacting an aqueous sample solution with the enhanced silver nanoparticle solution in such a manner as to allow the presence of a target analyte in the sample to be detected by surface enhanced Raman spectroscopy; and
    obtaining a surface enhanced Raman spectrum of the sample.

2. The method of claim 1 wherein the aqueous sample solution is contacted with the silver nanoparticles before the lithium chloride is added to the solution containing the silver nanoparticles.

3. The method of claim 1 wherein the aqueous sample solution is contacted with the silver nanoparticles after the lithium chloride is added to the solution containing the silver nanoparticles.

4. A method according to claim 1, wherein the target analyte is selected from the group consisting of amino acids, peptides, polypeptides, proteins, glycoproteins, lipoproteins, nucleosides, nucleotides, oligonucleotides, nucleic acids, carbohydrates, oligosaccharides, polysaccharides, lipids, hormones, neurotransmitters, antibodies, metabolites, cofactors, prions, toxins, pesticides, chemical warfare agents, bacteria, viruses, vitamins, carcinogens, mutagens, narcotics, amphetamines, barbiturates, hallucinogens, and mixtures thereof.

5. A method according to claim 1, wherein the target analyte is selected from the group consisting of amino acids, peptides, nucleosides, nucleotides, oligonucleotides, and mixtures thereof.

6. A method for analyzing a sample using surface enhanced Raman spectroscopy (SERS) comprising:
    providing a substrate comprising porous silicon having a metallic layer disposed on a surface of the porous silicon substrate, wherein the metallic layer covers at least part of the surface of the porous silicon substrate;
    activating the metallic layer using lithium chloride;
    contacting an aqueous solution comprising the sample to be analyzed with the activated metallic layer in such a manner as to allow the presence of a target analyte in the sample to be detected by surface enhanced Raman spectroscopy; and
    obtaining a surface enhanced Raman spectrum of the sample.

7. A method according to claim 6 wherein the porous silicon is nanocrystalline silicon.

8. The method of claim 6 wherein the metallic layer is comprised of a metal selected from the group consisting of silver, gold, aluminum, copper, platinum, and mixtures thereof.

9. The method of claim 6 wherein the metallic layer is comprised of silver.

10. The method of claim 6 wherein the metallic layer is comprised of metal nanoparticles.

11. The method of claim 6 wherein the metal layer is comprised of colloidal metal particles.

12. The method of claim 6 wherein the metallic layer is comprised of metal nanoparticles and a layer of metal overlying the metal nanoparticles.

13. The method of claim 10 wherein the metal nanoparticles are comprised of silver or gold.

14. The method of claim 10 wherein the metal nanoparticles are comprised of silver.

15. A method according to claim 6, wherein the target analyte is selected from the group consisting of amino acids, peptides, polypeptides, proteins, glycoproteins, lipoproteins, nucleosides, nucleotides, oligonucleotides, nucleic acids, carbohydrates, oligosaccharides, polysaccharides, lipids, hormones, neurotransmitters, antibodies, metabolites, cofactors, prions, toxins, pesticides, chemical warfare agents, bacteria, viruses, vitamins, narcotics, amphetamines, barbiturates, hallucinogens, and mixtures thereof.

16. The method of claim 6 wherein the target analyte is selected from the group consisting of amino acids, peptides, nucleosides, nucleotides, and oligonucleotides, and mixtures thereof.

* * * * *